United States Patent [19]
Chaudhari et al.

[11] Patent Number: 5,650,546
[45] Date of Patent: Jul. 22, 1997

[54] PROCESS FOR THE CATALYTIC HYDROGENATION OF ORGANIC COMPOUNDS

[75] Inventors: Raghunath Vitthal Chaudhari; Bhalchandra Mahadeo Bhanage; Sunil Sadashiv Divekar; Raj Madhukar Deshpande, all of Maharashtra, India

[73] Assignee: Council of Scientific Industrial Resear., New Delhi, India

[21] Appl. No.: 358,222

[22] Filed: Dec. 16, 1994

[51] Int. Cl.$^6$ .............................. C07C 5/10; C07C 29/14; C07C 49/62
[52] U.S. Cl. ...................... 585/269; 585/266; 568/434; 568/462; 568/881
[58] Field of Search .................... 524/709; 568/434, 568/451, 454, 462, 881; 556/15; 585/269, 266, 268

[56] References Cited

U.S. PATENT DOCUMENTS

| | | | |
|---|---|---|---|
| 3,511,880 | 5/1970 | Booth | 260/604 |
| 4,248,802 | 2/1981 | Kuntz . | |
| 4,517,390 | 5/1985 | Russell et al. | 585/269 |
| 4,778,905 | 10/1988 | Besson et al. | 556/16 |
| 5,003,110 | 3/1991 | Grosselin | 568/434 |
| 5,057,618 | 10/1991 | Herrmann et al. . | |
| 5,155,274 | 10/1992 | Herrmann et al. . | |
| 5,223,648 | 6/1993 | Herrmann et al. | 568/429 |
| 5,457,252 | 10/1995 | Gill et al. | 585/269 |
| 5,498,801 | 3/1996 | Chaudhari et al. | 568/454 |

OTHER PUBLICATIONS

Renaud et al., "Synthesis of a new family of water–soluble tertiary phosphine ligands and of their rhodium(I) complexes; olefin hydrogenation in aqueous and biphasic media", Journal of Organometallic Chemistry, 419 (1991) 403–415.

Smith et al., "Metal Carbonyl Derivatives of a Water Soluble Phosphine", Inorganica Chimica Acta, 62 (1982) 135–139.

Hablot et al., "Gas–Liquid–Liquid Reaction Using Water Soluble Catalyst", Chemical Engineering Science, vol. 47, No. 9–11, pp. 2689–2694, 1992.

Bailey et al., "Immobilized Transition–Metal Carbonyls and Related Catalysts", Chemical Reviews, vol. 81, No. 2, pp. 110–148, 1981.

Kalck et al., "Use of Water–Soluble Ligands in Homogeneous Catalysis", Advances in Organometallic Chemistry, vol. 34, pp. 219–284, 1992.

Primary Examiner—Glenn A. Caldarola
Assistant Examiner—Bekir L. Yildirim
Attorney, Agent, or Firm—Pennie & Edmonds LLP

[57] ABSTRACT

A process for the hydrogenation of organic compounds using water soluble catalyst in a biphasic media by: (A) forming an organo-water dispersion of (i) an organic phase having (a) an organic compound and (b) an organic solvent, and (ii) an aqueous phase having a water soluble group VIII metal catalyst composition and a water soluble ligand; and (B) contacting said dispersion with hydrogen to provide an interfacial reaction between said organic compound and said hydrogen, giving significant enhancement in the rate of reaction to produce saturated organic compound as compared to a reaction carried out in the absence of said water immiscible ligand.

18 Claims, No Drawings

PROCESS FOR THE CATALYTIC HYDROGENATION OF ORGANIC COMPOUNDS

FIELD OF THE INVENTION

The present invention relates to an improved process for the hydrogenation of organic compounds. The process is applicable for the hydrogenation of organic compounds consisting of one or more functional groups of the type alkyne, alkene, carbonyl (aldehydic, keto), nitro, nitroso, nitrile, nitrene etc. Specifically, the invention relates to a process for the hydrogenation of organic compounds using water soluble metal complex catalysts in the presence of a promoter in a water immiscible phase. The improved process results in the enhancement of the rate of hydrogenation by interfacial catalysis induced by the presence of a ligand (promoter) in a catalyst imscible phase.

The reaction system comprises of two phases viz— Organic phase and Aqueous phase. The organic phase consists of a substrate and an N- or P- containing water insoluble ligand with or without water immiscible solvent. The aqueous phase consists of a metal complex catalyst comprising of group VIII element such as Rh, Ru, Pd, Pt, Ir, Ni, Co, Fe, Os and a water soluble ligand of the type triphenylphosphine monosulfonate-sodium salt (TPPMS), triphenylphosphine disulfonate-sodium salt (TPPDS), triphenylphosphine trisulfonate-sodium salt (TPPTS), [2 (diphenyl phosphino) ethyl]trimethyl ammonium salt (amphos), [2 (diphenyl phosphino) ethyl]trimethyl phosphonium salt (phosphos) dissolved in water.

BACKGROUND OF THE INVENTION

The hydrogenated products have wide ranging applications in fine chemicals, pharmaceuticals and pertrochemical industries and this invention relates to a significant improvement in the catalytic process by interfacial catalysis, as illustrated by a variety of substrates with different functional groups.

Hydrogenation reactions are industrially important for the manufacture of a wide range of compounds. These products find applications in fine chemicals as well as intermediates in pharmaceutical and petrochemical industries. Hydrogenation reactions using homogeneous catalysis are well known in which addition of hydrogen to a substrate in the presence of a catalyst soluble in the reaction medium is involved. Although, this route has been applied commercially only in a few cases, it is of potential importance for systems where selectivity as well as activity are of prime importance. The major disadvantage in the use of homogeneous catalysis in hydrogenation is the difficulty in separation and isolation of the product from the catalyst solution and recycle/recovery processes.

To overcome these disdvantages various attempts were made to heterogenize these catalysts by binding the metal complex on supports like silica, polymer etc. These methods have so far not provided a commercially viable heterogeneous catalyst since loss of activity, selectivity, leaching, deactivation and decomposition of the catalyst is observed on repeated use (Kalck and Monteil in Adv. Organomet. chem 34, 219–284, 1992 and Bailey and Langer in Chem. Rev. 81, 109, 1981).

A major breakthrough in this direction has been the synthesis of water soluble phosphine ligands (E. Kuntz U.S. Pat. No. 4,248,802, 1981). These water soluble phosphine ligands are generally synthesized by introducing a hydrophilic group on the ligands. These phosphines generally occur in two major classes (1) Phosphines containing quarternized salt as the hydrophilic component e.g. (i) [2 (diphenyl phosphino) ethyl]trimethyl ammonium salt (amphos) (Smith & Baird in Inorg. Chim. Acta. 62,135, 1982) (ii) [2 (diphenyl phosphino) ethyl]trimethyl phosphonium salt (phosphos) (Renaud et. al. in J. organomet. chem. 419, 403, 1991) (2) Phosphines containing sulphonated groups as the hydrophilic component. Triphenyl phosphine monosulphonate sodium salt (TPPMS) and triphenyl phosphine trisulphonate sodium salt (TPPTS).

Besides these major classes, other modifications of phosphines find limited applications (Kalck and Monteil in Adv. Organomet. chem 34, 219–284, 1992 and reference cited therein). These ligands have been used for-the formation of water soluble complexes of transition metals. Such complexes are used as hydrogenation catalysts in two phase (aqueous/organic) systems. The system consists of an aqueous phase, comprising of the metal complex along with the water soluble ligand. The organic phase consists of a reactant with or without water immscible solvent. The reaction occurs in the aqueous phase with dissolved reactants. The products (usually water insoluble) separate out into the organic phase thus making product separation and catalyst recycle/recovery easy. The application of this methodology is, however, restricted to the substrates having marginal solubility in water. Due to a very low solubility of most of the organic compounds in the aqueous catalytic phase, the rates of reaction using these catalyst are significantly lower than the conventional homogeneously catalysed systems.

Use of a co-solvent has been advocated to overcome such limitations (I. Hablot Chem. Engg. Sci. 47, 2689 1992). This approach, however, does not prove to be very useful because of complications involving (i) reactivity of co-solvent (ii) enhanced solubility of water in the organic phase causing leaching of the catalyst (iii) large volumes of co-solvent required.

European patent EP 362037, 1990 deals with the preparation of saturated aldehydes from a, b-unsaturated aldehydes in a biphasic system using Rh catalyst and a water soluble ligand—TPPTS. The organic phase comprises of toluene alongwith the substrate.

Complexes of group VIIA VIIIA and IB elements with TPPTS and optional additional water soluble ligand were utilised for hydrogenation of different substrates in EP 372313, 1990. A $Co_2(CO)_8$/TPPTS catalyst system has been reported for hydrogenation of substrates like cyclohexene etc. in the same patent.

Complexes of group VIIIA elements with TPPTS ligand as hydrogenation catalyst are reported in German Patent DE 3840600, wherein $Rh(NO)(TPPTS)_3$ complex was used to hydrogenate cyclohexene and cyclooctene.

The hydrogenation catalysts described in the prior art using a biphasic system have a drawback of lower rates due to reactants solubility limitations in the aqueous phase.

SUMMARY OF THE INVENTION

The main objective of the present invention is to provide an improved process for the hydrogenation of organic compounds using a biphasic medium, to obtain higher rates of reaction. Another objective of present invention is to provide an improved process for the hydrogenation of organic compounds. Yet another objective of the present invention is to provide process for the hydrogenations of organic compounds in biphasic media, using water soluble catalysts comprising of group VIII metal complexes and substrates containing functional group like alkyne, alkene, carbonyl, (aldehydic, keto) nitro, nitroso, nitrile.

Still another objective of the present invention is to provide a hydrogenation process having enhanced rate of reaction without causing significant losses of the catalysts into the organic phase thereby retaining the activity and selectivity of the water soluble catalyst.

The main findings underlying the inventions can be summerized as follows:

It is observed that introduction of water insoluble ligand like tertiary aryl as well alkyl phosphines and phosphites into the organic phase causes significant enhancement in reaction rate in a biphasic catalytic hydrogenation. The presence of a ligand in the organic phase having negligible solubility in the aqueous phase results in substantial enriching the catalyst concentration at the liquid-liquid interface and hence results in dramatic enhancement in the rate of reaction.

The enhancement in the rate is obtained without affecting the liquid-liquid equilibria in significant way.

The improved process in the present invention has the following advantages over the processes described in the prior art:

Significant enhancement (2–100 times) in the rate of reaction of a biphasic catalytic hydrogenation as a result of interfacial catalysis.

Negligible or no loss of catalyst to organic phase by leaching.

Effective in absence or presence of aliphatic or aromatic solvents.

DETAILED DESCRIPTION OF THE INVENTION

The present invention is concerned with the modification of the conventional catalytic system for biphasic hydrogenation reactions.

The reaction system consists of two phases, Aqueous and organic (water immiscible). The organic phase comprises of a substrate with or without solvent (water immiscible) and water insoluble ligand. The aqueous phase consists of a catalyst containing group VIIIA metal along with water soluble ligand dissolved in the aqueous phase. The reaction is carried out by contacting hydrogen with the substrate and the catalyst in the aqueous-organic dispersion.

Examples of substrates that can be used as starting material consist of aliphatic or aromatic compounds containing one or more of the following functional groups alkyne, alkene, carbonyl, (aldehydic, keto) nitro, nitroso, nitriles (eg. butynediol diacetate, phenylacetylene, cyclohexene, octene, decene, tetradecene, hexadecene, heptaldehyde, valeraldehyde, benzaldehyde, benzophenone, acetophenone, methyl isobutyl ketone, cyclohexanone, nitrobenzene, o-nitrophenol, p-nitrophenol, o-nitroaniline, nitrosobenzene, nitrosophenol, adiponitrile, benzonitrile, crotonaldehyde, butyraldehyde, hexenal, 2-ethylhexenal, acrylonitrile, polybutadiene, etc.).

Examples of solvents immiscible in water which may be used in this invention include aliphatic and aromatic hydrocarbon solvents like hexane, heptane, octane, decane, benzene, toluene, o-, m-, p- xylene, cyclohexane, methylene chloride, ethylene chloride, ethyl acetate, diethyl ether, etc. However it is not a prerequisite for solvent to be utilised in the process of present invention.

Examples of water insoluble ligands added in the organic phase include N- or P- containing ligands of the type triphenyl phosphine, triphenyl phosphite, tributyl phosphine, tributyl phosphite, triethyl phosphine, triaryl and trialkyl phosphine, triaryl and trialkyl phosphites, and mixed phosphines i.e. alkyl-aryl-phosphines, trialkyl amines, triaryl amines. diphosphines, N- containing compounds like tertiary, secondary or primary amines, heterocycles, quinolines, substituted quinolines, pyridines etc.

The catalysts used in the process of present invention consist of water soluble metal complexes prepared from group VIIIA metals (eg. nickel, iron, cobalt, palladium, rhodium, platinum, ruthenium, iridium and osmium) or complexes of the said elements or compounds containing group VIII elements (eg. platinum metal carbonates, halides, sulphates, hydroxides, chlorates).

Examples of water soluble ligands which can be employed in the process of the invention can be of the type $PPh_n(C_6H_4SO_3M)_{3-n}$ (M=alkali metal, alkaline earth metal/ 2, quaternary ammonium group); n=0, 1 or 2. Water soluble phosphines containing qarternary ammonium group eg. amphos and phosphines containing phosphonium or acetate, hydroxyl groups.

The reaction may be carried out in the temperature range of 50°–150° C., preferably in the range of 80°–120° C. The hydrogen partial pressure used may vary between 5–2000 psig, most preferably between 100–600, psig. The hydrogen gas employed may be pure hydrogen as available commercially or may be contaminated with inert gases like nitrogen upto 10%. The molar ratio of group VIII element used as the catalyst to the water soluble ligands employed can be between 0.5 to 100 preferably between 1 to 20. The ratio of group VIII element used as the catalyst to the water insoluble ligand may vary between 0.01 to 50, Preferably between 0.1 to 5. The agitation speed employed for the reaction may vary between 300 to 2000, rpm. The phase holdup ratio employed may vary between 0.1 to 10 (aqueous to total liquid volume). The molar ratio of catalyst to substrate may vary between 1:5 to 1:8000 mol, preferably between 1:20 to 1:1000.

No process is hitherto known for the hydrogenation of organic compounds in which a dramatic increase in the rate of a biphasic catalytic reaction is reported through a interfacial catalysis.

The present invention is not limited to hydrogenation reactions as it can be extended for application to other similar biphasic catalytic reactions like hydroformylation, carbonylation, telomerization, metathesis, polymerization etc.

The process of the invention is described in detail in the examples given below that are presented by way of illustration only and should not be confined to limit the scope of the invention.

EXAMPLE 1

The following charge consisting of aqueous and organic phases was introduced in a 50 cc microclave equipped with magnetic drive type agitation system and connected to a reservoir of hydrogen under pressure.

The aqueous phase consisted of 0.025 g (0.05 mmol) of dirhodium dicyclooctadienyl dichloride $[Rh(C_8H_{12})Cl]_2$, representing 0.0001 g atom of Rh, was dissolved in deaerated water containing 500 mg of the trisodium salt of tris(sulfophenyl) phosphine (TPPTS) (0.664 mmol), and diluted to 10 cm$^3$ with deaerated water. The TPPTS was used from a stock solution of 50% w/w concentration in deaerated water. The molar ratio of Rh:TPPTS was 1:6. The organic phase consisted of 1-octene 10 cm3 (63.7 mmol) in the absence of any solvent along with triphenylphosphine 26 mg (0.1 mmol). The molar ratio of Rh:P was 1:1. The contents were heated upto 100° C. and the reaction was carried out at pH$_2$ of 400 psi and a stirring speed of 900 rpm. The reaction was carried out to completion. The reaction was over in 26 minutes. The activity moles of product form per grams of Rh per s of this reaction was found to be $1.63\times10^{-3}$ mol/s/g. The analysis of the reaction showed 99.8% conversion and 99.5% selectivity towards n-octane which is final product. In comparision the reaction taken in the absence of triphenyl phosphine in the organic phase (other charge is same as above) took 154 min for completion. This shows activity of $2.76\times10^{-4}$ mol/s/g. Conversion of this reaction was found to be 98.6% and selectivity of 99.0% towards final product i.e. n-octane.

EXAMPLE 2

The charge similar to that given in example 1 was taken except that 1-tetradecene 10 cm$^3$ (40.0 mmol) was taken instead of 1-octene. The reaction was completed in 26 minutes. The activity of this reaction was found to be $4.83\times10^{-4}$ mol/s/g. Conversion of this reaction was found to be 99.6% and selectivity of 98.2% towards final product tetradecane. A similar reaction taken in absence of triphenylphosphine took 90 minutes to go to completion, which shows the activity of $2.85\times10^{-4}$ mol/s/g. Conversion of this reaction was found to be 98.9% and selectivity of 97.4% towards final product n-tetradecane.

EXAMPLE 3

The charge similar to that given in example 2 was taken except that the tri-t-butylphosphine was used instead of triphenylphosphine in the same ratio of metal to phosphine. The reaction was completed in 9 minutes. This shows the activity of $3.90\times10^{-3}$ mol/s/g. Conversion of this reaction was found to 98.8% and selectivity of 99.1% towards final product n-tetradecane.

EXAMPLE 4

The charge similar to that given in example 2 was taken except that the tri-t-butylphosphite was used instead of triphenylphosphine in the same ratio of metal to phosphine. The reaction was completed in 23 minutes. The activity of this reaction was found to be $1.13\times10^{-3}$ mol/s/g. Conversion of this reaction was found to be 99.6% and selectivity of 98.3% towards final product n-tetradecane.

EXAMPLE 5

The charge similar to that given in example 2 was taken except that the tri-t-phenylphosphite was used instead of triphenylphosphine in the same ratio of metal to phosphine. The reaction was completed in 12 minutes. This shows the activity of $2.18\times10^{-3}$ mol/s/g. Conversion of thi reaction was found to be 99.1% and selectivity of 99.2% towards final product n-tetradecane.

EXAMPLE 6

A procedure similar to that indicated in example 1 was used. The following charge was taken. The aqueous phase consisted of RuCl$_3$.xH$_2$O 10.4 mg (0.1 mmol) equivalent of 0.0001 g atom of Ru dissolved in TPPTS solution containing 500 mg (0.664. mmol) of TPPTS. diluted to 10, cm$^3$ using deareated water. The organic phase consisted of 1-tetradecene 10, cm$^3$ (40.0, mmol) and tributylphosphine 0.05 mmol. The ratio of metal to phosphine used was 1:0.5. The condition and monitoring methodology were the same as in example 1. The reaction was found to go to completion in 15 min. The activity of this reaction was found to be $4.17\times10^{-3}$ mol/s/g. Conversion of this reaction was found to be 98.6% and selectivity of 99.1% towards n-tetradecane.

In comparision the reaction in absence to tributylphosphine went to completion in 135 min with the activity of $4.61\times10^{-4}$ mol/s/g. Conversion of this reaction was found to be 98.2% and selectivity of 99.1% towards n-tetradecane.

EXAMPLE 7

The charge similar to that given in example 6 was taken except that benzaldehde 10 cm$^3$ (98.4 mmol) was used for the reaction instead of 1-tetradecene and triphenylphosphine instead of tributylphosphine with metal to phosphine ratio of 1:1. The reaction was carried out for 120 minutes. Analysis of the organic phase showed 72% conversion of benzaldehyde with the selectivity of 95.6% to benzyl alcohol. The activity of this reaction was found be $9.05\times10^{-4}$ mol/s/g. For the same time the reaction conducted in the absence of triphenylphosphine showed only 38% conversion with benzyl alcohol selectivity of 94.8%. The acivity of this reaction is $4.7\times10^{-4}$ mol/s/g.

EXAMPLE 8

The procedure and methodology of monitoring the reaction as given in example 1 were used. The organic phase consisted of nitrobenzene 2.cm$^3$ (19.4 mmol) in toluene (13 cm$^3$) as a solvent along with triphenylphosphine 26.mg (0.1 mmol ). The reaction was found to go to completion in a period of 39, minutes. The activity of this reaction is $3.28\times10^{-4}$ mol/s/g. Conversion of this reaction was found to be 99.8% and selectivity of 99.2% towards aniline. Whereas, the reaction in the absence of triphenylphosphine took 95. minutes for completion. Conversion of this reaction was found to be 98.2% and selectivity of 99.1% towards aniline. The activity of this reaction is $1.32\times10^{-4}$ mol/s/g.

It is evident from these examples that the addition of a ligand/promoter in the organic phase causes a significant enhancement in the rate of the reaction by inducing an interfacial reaction. Besides the process of the reaction can be used for the hydrogenation of varierty of substrates as indicated above.

We claim:

1. A process for hydrogenation of unsaturated organic compounds comprising reacting unsaturated organic compounds with hydrogen using water soluble metal complex catalysts in a biphasic media comprising water and an organic medium to produce saturated organic compounds, wherein the improvement comprises inducing an interfacial reaction by adding a plurality of water immiscible promoters in the organic phase to impart a significantly enhanced rate of reaction by facilitating retention of the catalyst in the aqueous phase, wherein the water immiscible promoters are substantially insoluble in the aqueous phase.

2. A process as claimed in claim 1 wherein the unsaturated organic compound is selected from the group consisting of: a) open chain alkenes having 3 to 20 carbon atoms; b) styrenes and their corresponding alkyl benzenes; c) nitroaromatics and their corresponding amines; d) alkyl and aryl aldehydes and their corresponding alcohols; and e) alkyl, aryl or mixed alkyl-aryl ketones and their corresponding alcohols.

3. A process as claimed in claim 1 wherein the water soluble metal complex catalyst comprises at least one of a group VIII or group VIIIA element.

4. A process as claimed in claim 3 wherein the water soluble metal complex catalyst comprises an element selected from the group consisting of Fe, Co, Ni, Ru, Rh, Pd, Pt, and Ir, and mixtures and complexes thereof.

5. A process as claimed in claim 3 wherein the aqueous phase further contains a water soluble ligand selected from the group consisting of phosphines containing at least one sulfonated group, quaternary ammonium phosphines, quaternary phosphonium phosphines and mixtures thereof.

6. A process as claimed in claim 3, wherein the water soluble ligand has a formula of $PPh_n(C_6H_4SO_3M)_{3-n}$, wherein M is selected from the group consisting of an alkali metal, an alkaline earth metal, and a quaternary ammonium group, and n=0, 1 or 2.

7. A process as claimed in claim 1 wherein the water immiscible promoter is selected from the group consisting of $P-R_1R_2R_3$ or $P-(OR_1)$, $P-(OR_2)$, $P-(OR_3)$ diphosphines, amines and nitrogen containing heterocycles.

8. A process as claimed in claim 7 wherein said phosphorous containing water immiscible promoter comprises a phosphorous containing water insoluble ligand.

9. A process as claimed in claim 8 wherein said phosphorous containing water insoluble ligand is selected from the group consisting of triaryl phosphines, trialkyl phosphines, triaryl phosphites, trialkyl phosphites and mixed phosphines.

10. A process as claimed in claim 1 wherein the temperature ranges from 50° to 150° C.

11. A process as claimed in claim 10 wherein the temperature ranges from 80° C. to 120° C.

12. A process as claimed in claim 1 wherein the hydrogen pressure ranges from 5 to 2000 psi.

13. A process as claimed in claim 12 wherein the hydrogen pressure ranges from 100 to 600 psi.

14. A process as claimed in claim 1 wherein the molar ratio of catalyst to substrate varies between 1:5 to 1:8000 mol.

15. A process as claimed in claim 1 wherein the molar ratio of catalyst to water soluble ligand to water immiscible promoter ranges from 1:0.5:0.001 to 1:100:50.

16. A process as claimed in claim 15 wherein the molar ratio of catalyst to water soluble ligand to water immiscible promoter ranges from 1:1:1 to 1:20:5.

17. A process for the hydrogenation of organic compounds using water soluble catalyst in a biphasic media comprising:
   a) forming an organo-water dispersion of
      i) an organic phase comprising (A) an organic compound, (B) an organic solvent, and (C) at least one water immiscible promoter; and
      ii) an aqueous phase comprising a water soluble group VIII metal catalyst composition and a water soluble ligand, wherein the water immiscible promoter is substantially insoluble in the aqueous phase
   b) providing hydrogen to said dispersion for an interfacial reaction with said organic compound and to provide an enhanced rate of reaction to produce saturated organic compounds as compared to a reaction carried out in the absence of said water immiscible promoter.

18. A process for hydrogenation of organic compounds comprising reacting organic compounds with hydrogen using water soluble catalysts in a biphasic media comprising water and an organic medium to produce saturated organic compounds, wherein the improvement comprises inducing an interfacial reaction by adding a plurality of water immiscible promoters in the organic phase to impart a significantly enhanced rate of reaction, wherein the water immiscible promoters are substantially insoluble in the aqueous phase, facilitate retention of the catalyst in the aqueous phase, and are each a P-containing ligand selected from the group consisting of $P-R_1R_2R_3$, $P-(OR_1)$, $(OR_2)$, and $(OR_3)_3$, wherein $R_1$, $R_2$, and $R_3$ are alkyl aryl groups; diphosphines; N-containing ligands selected from the group consisting of diamines, tertiary or secondary amines, quinolines, pyridines, and lutidines; N-containing heterocycles; and substituted derivatives thereof.

* * * * *